PYRIDAZINONES AS PESTICIDES

[75] Inventors: Joachim Weissmüller, Monheim; Klaus-Günther Tietjen, Langenfeld; Wilhelm Stendel, Wuppertal; Ulrike Wachendorff-Neumann, Leverkusen, all of Fed. Rep. of Germany

[73] Assignee: Bayer Aktiengesellschaft, Leverkusen, Fed. Rep. of Germany

[21] Appl. No.: 440,544

[22] Filed: Nov. 22, 1989

[30] Foreign Application Priority Data

Dec. 13, 1988 [DE] Fed. Rep. of Germany ....... 3841850
Jul. 18, 1989 [DE] Fed. Rep. of Germany ....... 3923659

[51] Int. Cl.$^5$ .................. A01N 43/58; C07D 401/00; C07D 237/00
[52] U.S. Cl. .................................. 514/247; 514/253; 544/238; 544/240
[58] Field of Search ................ 544/238, 240; 514/253, 514/247

[56] References Cited

U.S. PATENT DOCUMENTS 4,868,300  9/1989  Kuhla et al. ...................... 544/238

FOREIGN PATENT DOCUMENTS 0134439  3/1985  European Pat. Off. ............ 544/238
0232825  8/1987  European Pat. Off. ............ 544/240

Primary Examiner—Mary C. Lee
Assistant Examiner—Robert C. Whittenbaugh
Attorney, Agent, or Firm—Sprung, Horn, Kramer & Woods

[57] ABSTRACT

Pesticidal substituted pyridazinones of the formula

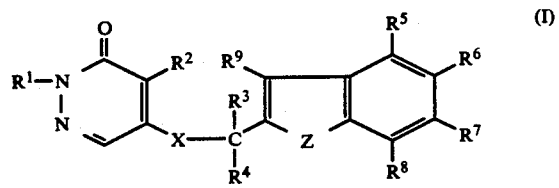

in which
$R^1$ represents alkyl or halogenoalkyl, or represents optionally substituted cycloalkyl, or represents optionally substituted cycloalkylalkyl, or represents optionally substituted aralkyl,
$R^2$ represents halogen or alkyl,
$R^3$ and $R^4$ independently of one another each represents hydrogen or alkyl,
$R^5$, $R^6$, $R^7$, $R^8$ and $R^9$ independently of one another each represents hydrogen, halogen, alkyl, halogenoalkyl, alkoxy, halogenoalkoxy, alkylthio or halogenoalkylthio,
X represents oxygen or sulphur and
Z represents a radical of the formula —CH=CH—, —CH$_2$—O—, —O— or —S—.

7 Claims, No Drawings

PYRIDAZINONES AS PESTICIDES

The invention relates to new substituted pyridazinones, to a plurality of processes for their preparation, and to their use as pesticides.

It is known that certain substituted pyridazinones, such as, for example, the compound 2-t-butyl-4-chloro-5-{2-[4-(3,3-dimethylbutyl)-2,6-dichlorophenoxy]ethylthio}-pyridazin-(2H)-3-one, the compound 2-t-butyl-4-chloro-5-(4-t-butyl-phenylmethylthio)-3(2H)-pyridazinone or the compound 2-t-butyl-4-chloro-5-[2-(4-methyl-2,6-dichlorophenoxy)-ethylthio]-pyridazin-(2H)-3-one, have a good activity against pests, in particular a good insecticidal, acaricidal, nematicidal and fungicidal activity (cf., for example, European Patent 232,825 and European Patent 134,439).

However, the level of effectiveness and duration of effectiveness of these previously known compounds is not entirely satisfactory in all fields of application, in particular when applied against certain organisms or at low application concentrations.

New substituted pyridazinones of the general formula (I)

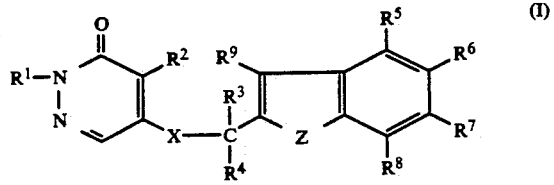

in which
R$^1$ represents alkyl or halogenoalkyl, or represents optionally substituted cycloalkyl, or represents optionally substituted cycloalkylalkyl, or represents optionally substituted aralkyl,
R$^2$ represents halogen or alkyl,
R$^3$ and R$^4$ independently of one another each represents hydrogen or alkyl,
R$^5$, R$^6$, R$^7$, R$^8$ and R$^9$ independently of one another each represents hydrogen, halogen, alkyl, halogenoalkyl, alkoxy, halogenoalkoxy, alkylthio or halogenoalkylthio,
X represents oxygen or sulphur and
Z represents a radical of the formula —CH=CH—, —CH$_2$—O—, —O— or —S—,
have been found.

Furthermore, it has been found that the new substituted pyridazinones of the general formula (I)

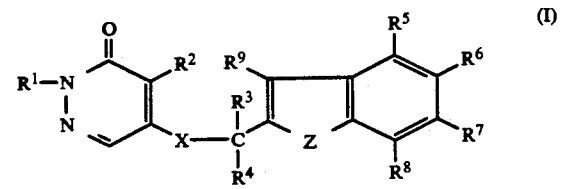

in which
R$^1$ represents alkyl or halogenoalkyl, or represents optionally substituted cycloalkyl, or represents optionally substituted cycloalkylalkyl, or represents optionally substituted aralkyl,
R$^2$ represents halogen or alkyl,
R$^3$ and R$^4$ independently of one another each represents hydrogen or alkyl,
R$^5$, R$^6$, R$^7$, R$^8$ and R$^9$ independently of one another each represents hydrogen, halogen, alkyl, halogenoalkyl, alkoxy, halogenoalkoxy, alkylthio or halogenoalkylthio,
X represents oxygen or sulphur and
Z represents a radical of the formula —CH=CH—, —CH$_2$—O—, —O— or —S—,
are obtained when
(a) 5-hydroxy- or 5-mercaptopyridazinones of the formula (II)

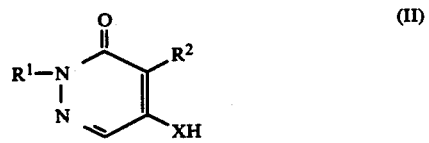

in which X, R$^1$ and R$^2$ have the abovementioned meanings, are reacted with alkylating agents of the formula (III)

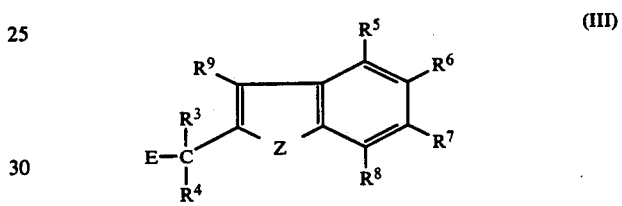

in which
E represents an electron-withdrawing leaving group and
R$^3$, R$^4$, R$^5$, R$^6$, R$^7$, R$^8$, R$^9$ and Z have the above-mentioned meanings,
if appropriate in the presence of a diluent and if appropriate in the presence of a reaction auxiliary, or when
(b) 5-chloropyridazinones of the formula (IV)

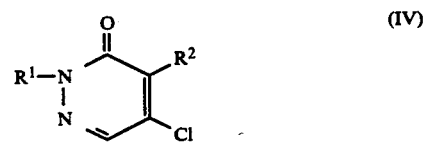

in which R$^1$ and R$^2$ have the abovementioned meanings, are reacted with aralkyl alcohols or aralkyl thiols of the formula (V)

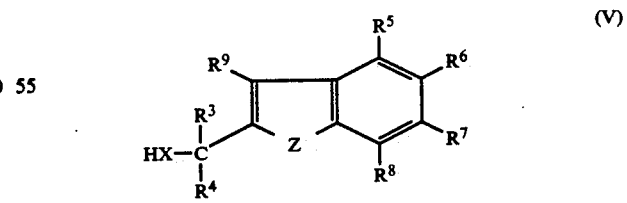

in which R$^3$, R$^4$, R$^5$, R$^6$, R$^7$, R$^8$, R$^9$, X and Z have the above-mentioned meanings,
if appropriate in the presence of a diluent and if appropriate in the presence of a reaction auxiliary.

Finally, it has been found that the new substituted pyridazinones of the general formula (I) have a good activity against pests, in particular a good insecticidal, acaricidal and ovicidal activity.

Surprisingly, the substituted pyridazinones according to the invention show a considerably better insecticidal activity against insects and arachnids which damage plants and parasitize warm-blooded animals, and additionally have a better ovicidal action, than the substituted pyridazinones which are known from the prior art, such as, for example, the compound 2-t-butyl-4-chloro-5-{2-[4-(3,3-dimethylbutyl)-2,6-dichlorophenoxyl]ethylthio}-pyridazin-(2H)-3-one, the compound 2-t-butyl-4-chloro-5-(4-t-butyl-phenylmethylthio)-3(2H)-pyridazin-one or the compound 2-t-butyl-4-chloro-5-[2-(4-methyl-2,6-dichlorophenoxy)-ethylthio]-pyridazin-3(2H)-one, which are chemically similar compounds of a similar type of action.

Formula (I) provides a general definition of the substituted pyridazinones according to the invention. Preferred compounds of the formula (I) are those in which $R^1$ represents straight-chain or branched alkyl having 1 to 8 carbon atoms, or represents straight-chain or branched halogenoalkyl having 1 to 6 carbon atoms and 1 to 13 identical or different halogen atoms, or represents cycloalkyl which has 3 to 7 carbon atoms or cycloalkylalkyl which has 3 to 7 carbon atoms in the cycloalkyl moiety and 1 to 4 carbon atoms in the straight-chain or branched alkyl moiety, each of which is optionally monosubstituted or polysubstituted by identical or different substituents, suitable substituents in the cycloalkyl moiety in each case being: alkyl having 1 to 4 carbon atoms, or halogen; $R^1$ furthermore represents aralkyl which has 6 to 10 carbon atoms in the aryl moiety and 1 to 4 carbon atoms in the straight-chain or branched alkyl moiety and which is optionally monosubstituted or polysubstituted by identical or different substituents, suitable aryl substituents being: halogen, cyano, nitro, in each case straight-chain or branched alkyl, alkoxy or alkylthio, each of which has 1 to 4 carbon atoms, or in each case straight-chain or branched halogenoalkyl, halogenoalkoxy or halogenoalkylthio, each of which has 1 to 4 carbon atoms and 1 to 9 identical or different halogen atoms, $R^2$ represents chlorine, bromine or iodine, or represents straight-chain or branched alkyl having 1 to 4 carbon atoms, $R^3$ and $R^4$ independently of one another each represents hydrogen, or represents straight-chain or branched alkyl having 1 to 4 carbon atoms, $R^5$, $R^6$, $R^7$, $R^8$ and $R^9$ independently of one another each represents hydrogen or halogen or represents in each case straight-chain or branched alkyl, alkoxy or alkylthio, each of which has 1 to 4 carbon atoms, or represents in each case straight-chain or branched halogenoalkyl, halogenoalkoxy or halogenoalkylthio, each of which has 1 to 4 carbon atoms and each of which has 1 to 9 identical or different halogen atoms, X represents oxygen or sulphur and Z represents a radical of the formula —CH=CH—, —CH$_2$—O—, —O— or —S—.

Particularly preferred compounds of the formula (I) are those in which $R^1$ represents methyl, ethyl, n- or i-propyl or n-, i-, s- or t-butyl, or represents straight-chain or branched pentyl, or represents straight-chain or branched hexyl, or represents straight-chain or branched fluoroalkyl having 1 to 4 carbon atoms and 1 to 5 fluorine atoms, or represents cyclopropyl, cyclopentyl, cyclohexyl, cyclopropylmethyl, cyclopropylethyl, cyclopropylpropyl or cyclohexylmethyl, each of which is optionally monosubstituted to pentasubstituted by identical or different substituents from the series comprising fluorine, chlorine, methyl and/or ethyl, or represents benzyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n-or i-propoxy, methylthio, trifluoromethyl, trifluoromethoxy, difluoromethoxy or trifluoromethylthio, $R^2$ represents fluorine, chlorine, bromine, methyl, ethyl or n- or i-propyl, $R^3$ and $R^4$ independently of one another each represents hydrogen, methyl or ethyl, $R^5$, $R^6$, $R^7$, $R^8$ and $R^9$ independently of one another each represents hydrogen, fluorine, chlorine, bromine, iodine, methyl, ethyl, n- or i-propyl, n-, i-, s- or t-butyl, trifluoromethyl, trifluoromethoxy, difluoromethoxy, trifluoromethylthio, methoxy, ethoxy or methylthio, X represents oxygen or sulphur and Z represents a radical of the formula —CH=CH—, —CH$_2$—O—, —O— or —S—.

Very particularly preferred compounds of the formula (I) are those in which $R^1$ represents methyl, ethyl, i-propyl, i-butyl, t-butyl, i-amyl, t-amyl, difluoro-t-butyl or trifluoro-t-butyl, or represents cyclopentyl or cyclohexyl, or represents cyclopropylmethyl or cyclopropylethyl, each of which is optionally monosubstituted to pentasubstituted by identical or different substituents from the series comprising fluorine, chlorine and/or methyl, or represents benzyl which is optionally monosubstituted or disubstituted by identical or different substituents from the series comprising fluorine, chlorine, bromine, methyl, ethyl, methoxy, methylthio, trifluoromethyl, trifluoromethoxy, difluoromethoxy or trifluoromethylthio, $R^2$ represents chlorine, bromine, methyl or ethyl, $R^3$ and $R^4$ independently of one another each represent hydrogen or methyl, $R^5$, $R^6$, $R^7$, $R^8$ and $R^9$ independently of one another each represents hydrogen, fluorine, chlorine, bromine, methyl, ethyl, n- or i-, s- or t-butyl, trifluoromethyl, trifluoromethoxy, difluoromethoxy, trifluoromethylthio, methoxy or ethoxy, X represents oxygen or sulphur and Z represents a radical of the formula —CH=CH—, —CH$_2$—O—, —O— or —S—.

Particularly preferred compounds of the formula (I) are those in which $R^1$ represents methyl, ethyl, i-propyl, i-butyl, t-butyl, i-amyl, t-amyl, difluoro-t-butyl or trifluoro-t-butyl, or cyclopentyl or cyclohexyl, or cyclpropylmethyl or cyclopropylethyl which are in each case optionally mono-to pentasubstituted by identical or different substituents from amongst fluorine, chlorine and/or methyl, or benzyl which is optionally mono- or disubstituted by identical or different substituents from amongst fluorine, chlorine, bromine, methyl, ethyl, methoxy, methylthio, trifluoromethyl, trifluoromethoxy, difluoromethoxy and/or trifluoromethylthio, $R^2$ represents chlorine, bromine, methyl or ethyl, $R^3$ and $R^4$ independently of one another in each case represents hydrogen or methyl, $R^5$, $R^6$, $R^7$, $R^8$ and $R^9$ independently of one another in each case represents hydrogen, fluorine, chlorine, bromine, methyl, ethyl, n- or i-, s- or t-butyl, trifluoromethyl, trifluoromethoxy, difluoromethoxy, trifluoromethylthio, methoxy or ethoxy, X represents oxygen or sulphur and Z represents a radical of the formula —CH$_2$—O—.
The following substituted pyridazinones of the general formula (I)
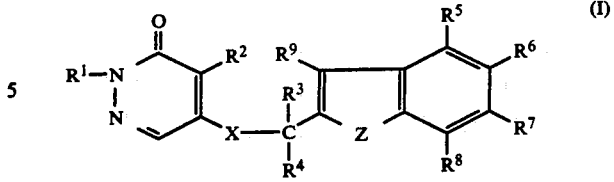
may be mentioned individually in addition to the compounds mentioned in the Preparation Examples:
| R$^1$ | R$^2$ | R$^3$ | R$^4$ | X | 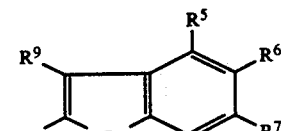 |
|---|---|---|---|---|---|
| (CH$_3$)$_3$C— | Cl | H | H | S | 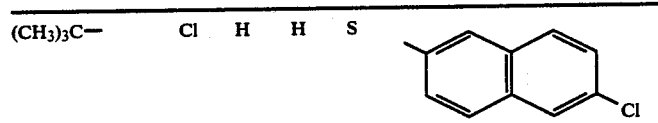 |
| (CH$_3$)$_3$C— | Cl | H | H | S |  |
| (CH$_3$)$_3$C— | Cl | H | H | S |  |
| (CH$_3$)$_3$C— | Cl | H | H | S | 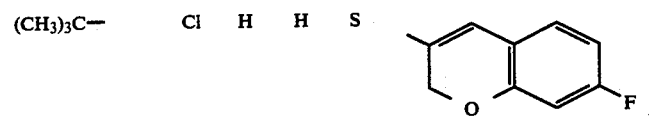 |
| (CH$_3$)$_3$C— | Cl | H | H | S | 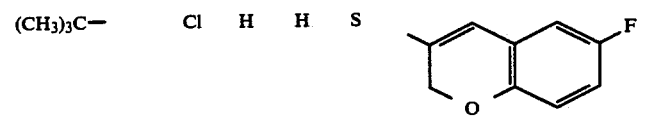 |
| 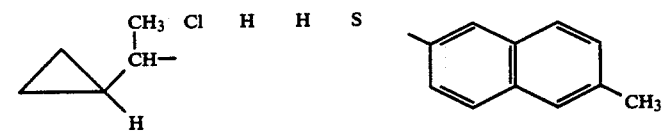 | Cl | H | H | S | |
|  | Cl | H | H | S | |
| 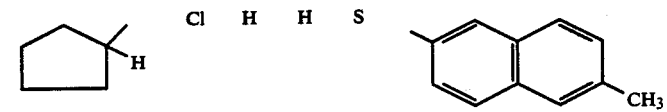 | Cl | H | H | S | |
| 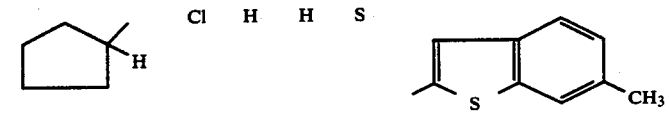 | Cl | H | H | S | |

-continued

| R¹ | R² | R³ | R⁴ | X | (aryl group with R⁵,R⁶,R⁷,R⁸,R⁹,Z) |
|---|---|---|---|---|---|
| 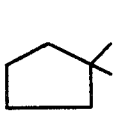 (cyclopentyl-CH(CH₃)-) | Cl | H | H | S | 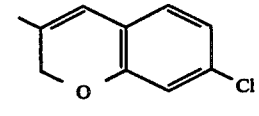 7-Cl chromene |
| (CH₃)₃C— | Cl | H | H | S | 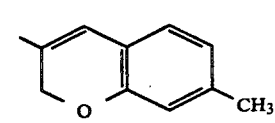 7-CH₃ chromene |
| (CH₃)₃C— | Cl | H | H | S |  6-CH₃ benzothiophene |
| (CH₃)₃C— | Cl | H | H | S | 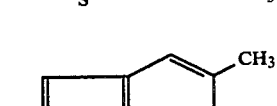 5-CH₃ benzothiophene |
| (CH₃)₃C— | Cl | H | H | S | 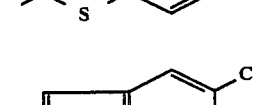 5-Cl benzothiophene |
| (CH₃)₃C— | Cl | H | H | S | 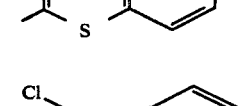 3-Cl benzothiophene |
| (CH₃)₃C— | Cl | H | H | S | 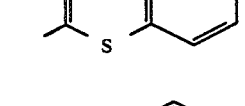 C(CH₃)₃ benzothiophene |
| (CH₃)₃C— | Cl | H | H | S | 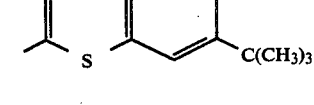 naphthyl-OCHF₂ |
| (CH₃)₃C— | Cl | H | H | S | 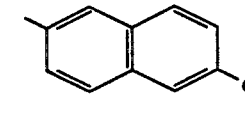 naphthyl-OCF₃ |
| (CH₃)₃C— | Cl | H | H | S | 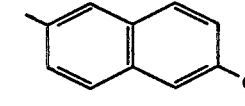 naphthyl-CF₃ |
| (CH₃)₃C— | Cl | H | H | S | 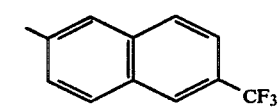 naphthyl-OC₂H₅ |

-continued

| R¹ | R² | R³ | R⁴ | X | 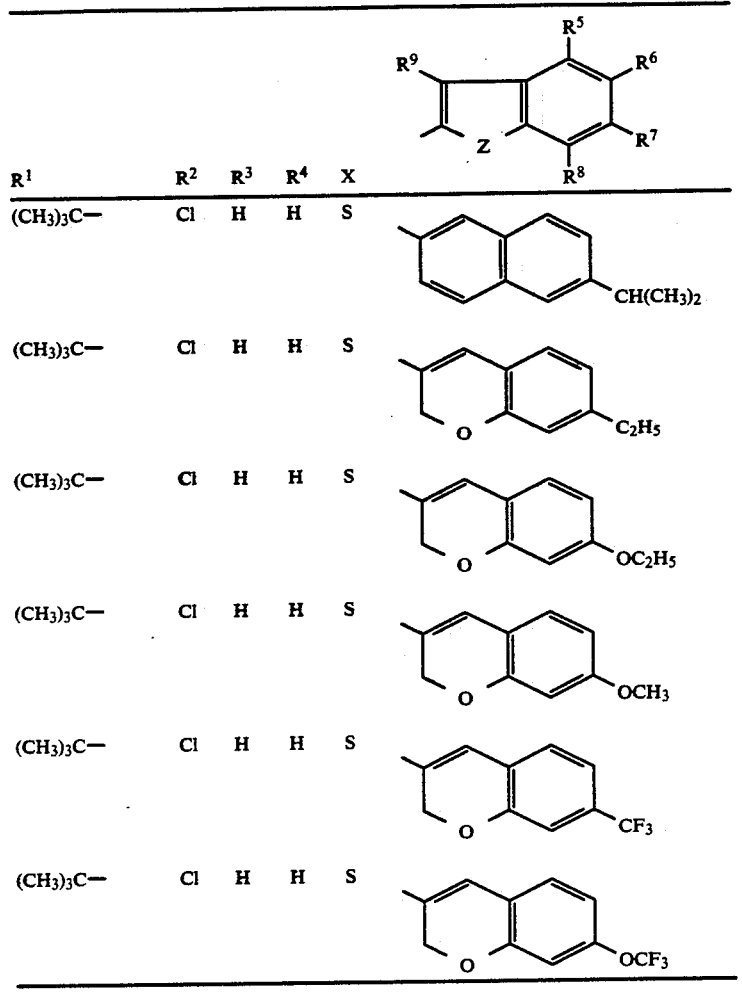 |
|---|---|---|---|---|---|
| (CH₃)₃C— | Cl | H | H | S | 6-isopropyl-2-naphthyl |
| (CH₃)₃C— | Cl | H | H | S | 6-ethyl-2H-chromen-3-yl |
| (CH₃)₃C— | Cl | H | H | S | 6-ethoxy-2H-chromen-3-yl |
| (CH₃)₃C— | Cl | H | H | S | 6-methoxy-2H-chromen-3-yl |
| (CH₃)₃C— | Cl | H | H | S | 6-trifluoromethyl-2H-chromen-3-yl |
| (CH₃)₃C— | Cl | H | H | S | 6-trifluoromethoxy-2H-chromen-3-yl |

If, for example, 2-t-butyl-4-chloro-5-hydroxypyridazin-3-(2H)-one and 2-bromomethyl-6-methylnaphthalene are used as starting substances, the course of the reaction of process (a) according to the invention may be represented by the following equation:

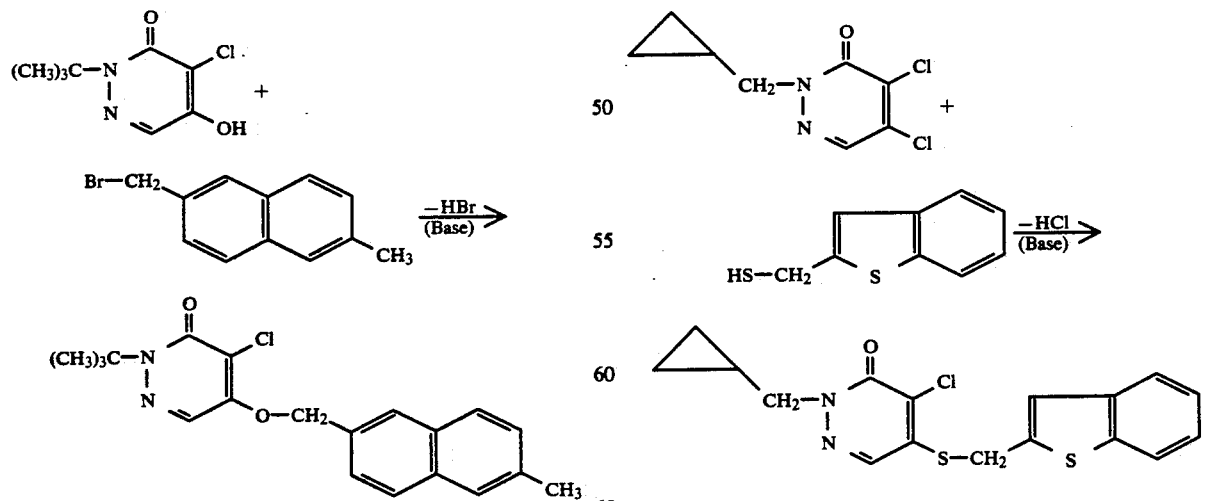

If, for example, 2-cyclopropylmethyl-4,5-dichloropyridazin-3-(2H)-one and 2-mercaptomethylbenzthiophene are used as starting substances, the course of the reaction of process (b) according to the invention may be represented by the following equation:

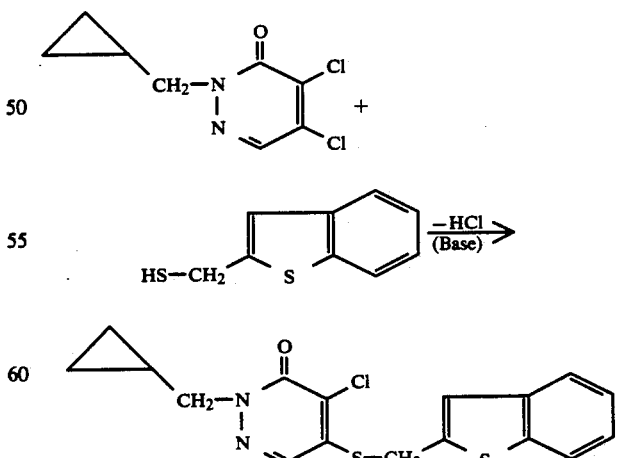

Formula (II) provides a general definition of the 5-hydroxy- or 5-mercaptopyridazinones required as starting substances for carrying out process (a) according to the invention. In this formula (II), R¹, R² and X preferably represent those radicals which have already been mentioned in connection with the description of the substances of the formula (I) according to the invention as being preferred for these substituents.

The 5-hydroxy- and 5-mercaptopyridazinones of the formula (II) are known or can be obtained in analogy with known processes (cf., for example, European Patent 199,281; European Patent 183,212; Chem. Pharm. Bull. 18, 147–156 [1979]; Japanese Patent 61/109777; Heterocycles 26, 1–4 [1987]; Pestic. Sci. 9, 571–581 [1978]; Chem. Zvesti 30, 663–673 [1976]or CA 87: 135236y; CS 146,172 dated 15.12.1972).

Formula (III) provides a general definition of the aralkylating agents furthermore required as starting substances for carrying out process (a) according to the invention. In this formula (III), $R^3$, $R^4$, $R^5$, $R^6$, $R^7$, $R^8$, $R^9$ and Z preferably represent those radicals which have already been mentioned in connection with the description of the substances of the formula (I) according to the invention as being preferred for these substituents.

E represents a leaving group customary in the case of alkylating agents, and preferably represents halogen, in particular represents chlorine, bromine or iodine, or represents in each case optionally substituted alkylsulphonyloxy, alkoxysulphonyloxy or arylsulphonyloxy, such as, in particular, methanesulphonyloxy, trifluoromethanesulphonyloxy, methoxysulphonyloxy, ethoxysulphonyloxy or p-toluenesulphonyloxy.

The alkylating agents of the formula (III a)

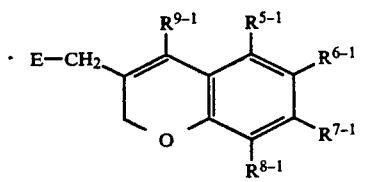

in which
$R^{5-1}$, $R^{6-1}$, $R^{7-1}$, $R^{8-1}$ and $R^{9-1}$ independently of one another in each case represent hydrogen; halogen, such as preferably fluorine, chlorine or bromine; alkyl, alkoxy or alkylthio which are in each case straight-chained or branched and in each case have 1 to 4 carbon atoms, such as preferably methyl, ethyl, n-, i-, s- or t-butyl, methoxy, ethoxy or methylthio; and halogenoalkyl, halogenoalkoxy or halogenoalkylthio which are in each case straight-chained or branched and in each case have 1 to 4 carbon atoms and in each case I to 9 identical or different halogen atoms, such as preferably trifluoromethyl, trifluoromethoxy, difluoromethoxy or trifluoromethylthio; with the proviso, however, that the substituents do not all represent hydrogen at the same time; and E represents halogen, such as preferably chlorine, bromine or iodine, and in each case optionally substituted alkylsulfonyloxy, alkoxysulphonyloxy or arylsulphonyloxy, such as preferably methanesulphonyloxy, trifluoromethanesulphonyloxy, methoxy-sulphonyloxy, ethoxysulphonyloxy or p-toluenesulphonyloxy, have not hitherto been disclosed.

The alkulating agents of the formula (IIIa) are obtained in analogy to generally known processes by reacting corresponding alcohols of the formula (Va)

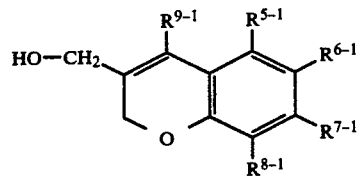

in which $R^{5-1}$, $R^{6-1}$, $R^{8-1}$ and $R^{9-1}$ independently of one another in each case represent hydrogen; halogen, such as preferably fluorine, chlorine or bromine; alkyl, alkoxy or alkythio which are in each case straight-chained or branched and in each case have to 4 carbon atoms, such as preferably methyl, ethyl, n-, i-, s- or t-butyl, methoxy, ethoxy or methylthio; and halogenoalkyl, halogenoalkoxy or halogenoalkythio which are in each case straight-chained or branched and in each case have 1 to 4 carbon atoms and in each case 1 to 9 identical or different halogen atoms, such as preferably trifluoromethyl, trifluoromethoxy, difluoromethoxy or trifluoromethylthio; with the proviso, however, that the substituents do not all represent hydrogen at the same time; with appropriate halogenating or sulphonylating agents (cf. also the preparative examples).

The alcohols of the formula (Va) have also not hitherto been disclosed. They are also obtained in analogy to generally known processes by reducing corresponding 2(H)-chromene-3-carboxylic acids of the formula (VI)

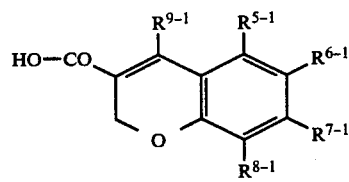

in which $R^{5-1}$, $R^{6-1}$, $R^{7-1}$, $R^{8-1}$ and $R^{9-1}$ have the above mentioned meanings, or corresponding 2(H)-chromene-3-carbaldehydes of the formula (VII)

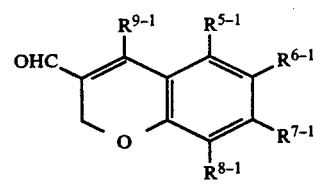

in which $R^{5-1}$, $R^{6-1}$, $R^{7-1}$, $R^{8-1}$ and $R^{9-1}$ have the above mentioned meanings, preferably with the aid of sodium borohydride or lithium aluminum hydride (cf. also the preparative examples).

The 2(H)-chromene-3-carboxylic acids of the formula (VI) and the 2(H)-chromene-3-carbaldehydes of the formula (VII) are known (cf. for example J.Org.-Chem.39, 2425 (1974) or can be prepared in an analogous manner.

The alkylating agents of the formula (III) are generally known compounds or can be obtained in analogy with generally known processes of organic chemistry (cf., for example, U.S. Pat. No. 4,282,227; DE-OS (German Published Specification) 2,508,335; European Patent 221,677; Eur. J. med. Chem. 22, 539–544 [1987]; U.S. Pat. No. 3,790,600; DE-OS (German Published Specification) 2,317,106; J. org. Chem. 53, 3634–3637 [1988]).

Formula (IV) provides a general definition of the 5-chloropyridazinones required as starting substances for carrying out process (b) according to the invention. In this formula (IV), $R^1$ and $R^2$ preferably represent those radicals which have already been mentioned in connection with the description of the substances of the formula (I) according to the invention as being preferred for these substituents.

The 5-chloropyridazinones of the formula (IV) are known or can be obtained in analogy with known processes (cf., for example, European Patent 169,375; Chem. Zvesti 38, 239–246 [1984]or CA 101: 110848u; GB 2,095,669; Synthesis 1981, 631–633.)

Formula (V) provides a general definition of the aralkyl alcohols and aralkyl thiols furthermore required as starting substances for carrying out process (b) according to the invention. In this formula (V), $R^3$, $R^4$, $R^5$, $R^6$, $R^7$, $R^8$, $R^9$, X and Z preferably represent those radicals which have already been mentioned in connection with the description of the substances of the formula (I) according to the invention as being preferred for these substituents.

The aralkyl alcohols and aralkyl thiols of the formula (V) are generally known compounds or can be obtained in analogy with generally known processes of organic chemistry (cf., for example, DE-OS (German Published Specification) 2,317,106; U.S. Pat. No. 3,790,600; J. Am. Chem. Soc. 106, 1779–1789 [1984]; Synthesis 1987, 647–648; Japanese Patent 62/87529; Eur. J. Med. Chem. 22, 539–544 [1987]; J. Heterocycl. Chem. 23, 1211–1214 [1986]; J. Chem. Soc. Perkin Trans. 1, 1972, 787–792).

Suitable diluents for carrying out processes (a) and (b) according to the invention are inert organic solvents. These in particular include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

If appropriate, processes (a) and (b) according to the invention can also be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyl-dimethyl-ammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride, trimethyl-benzylammonium chloride or tris-[2-(2-methoxyethoxy)-ethyl]-amine.

Processes (a) and (b) according to the invention are preferably carried out in the presence of a suitable reaction auxiliary. Suitable reaction auxiliaries are all inorganic and organic bases which can customarily be used. The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU), are preferably used.

When carrying out processes (a) and (b) according to the invention, the reaction temperatures can be varied within a substantial range. In general, the process is carried out at temperatures between 0° C. and 150° C., preferably at temperatures between 20° C. and 120° C.

For carrying out process (a) according to the invention, 1.0 to 5.0 moles, preferably 1.0 to 3.0 moles, of aralkylating agent of the formula (III) and, if appropriate, 1.0 to 5.0 moles, preferably 1.0 to 3.0 moles, of reaction auxiliary are generally employed per mole of 5-hydroxy- or 5-mercaptopyridazinone of the formula (II).

The reaction is carried out and the reaction products are worked up and isolated by generally customary methods (cf. also the Preparation Examples).

For carrying out process (b) according to the invention, 1.0 to 5.0 moles, preferably 1.0 to 3.0 moles, of aralkyl alcohol or aralkyl thiol of the formula (V) and, if appropriate, 1.0 to 5.0 moles, preferably 1.0 to 3.0 moles, of reaction auxiliary are generally employed per mole of 5-chloropyridazinone of the formula (IV).

The reaction is carried out and the reaction products are worked up and isolated by generally customary methods.

The active compounds are suitable for combating animal pests, preferably arthropods and nematodes and in particular insects, arachnida encountered in agriculture, in animal keeping, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta* americana, Leucophaea maderae, Blattella germanica, *Acheta domesticus*, Gryllotalpa spp., *Locusta migratoria migratorioides, Melanoplus differentralis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix* Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., Dysdercus intermedius, Piesma quadrata, Cimex *lectularius, Rhodnius prolixus* and Triatoma spp. From the order of the Homoptera, for example, *Aleurodes brassicae*, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus *arundinis, Macrosiphum avenae,* Myzus spp., *Phorodon humuli, Rhopalosiphum padi,* Empoasca spp., *Euscelis* bilobatus, Nephotettix cincticeps, Lecanium corni, Saissetia oleae, Laodelphax striatellus, Nilaparvata *lugens, Aonidiella aurantii, Aspidiotus hederae,* Pseudococcus spp. Psylla spp. From the order of the Lepidoptera, for example, *Pectinophora gossypiella, Bupalus* piniarius, Cheimatobia brumata, Lithocolletis blancardella, Hyponomeuta padella, Plutella maculipennis, *Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria* mellonea, Tineola bisselliella, Trnea pellionella, Hofmannophila pseudospretella, Cacoecia podana, Capua reticulana, Choristoneura fumiferana, Clysia ambiguella, *Homona magnanima* and *Tortrix viridana.* From the order of the Coleoptera, for example, *Anobium punctatum, Rhizopertha* dominica, Acanthoscelides obtectus, Acanthoscelides obtectus, Hylotrupes bajulus, Agelastica alni, *Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Hydrotaea spp., Haematobia spp., Glossina spp., Melophagus spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp , Tabanus spp., Tannia spp., *Bibio hortulanus, Oscinella frit,* Phorbia spp., *Pegomyia hyoscyami,* Ceratitis capitata, Dacus oleae and Tipula paludosa.

From the order of the Siphonaptera, for example, *Xenopsylla cheopis,* Ceratophyllus spp. and Ctenocephalides spp.. From the order of the Arachnida, for example, *Scorpio maurus* and *Latrodectus mactans.*

From the order of the Acarina, for example, *Acarus siro,* Argas spp., Ornithodoros spp., *Dermanyssus gallinae,* Ornithonyssus spp., *Eriophyes ribis, Phyllocoptruta oleivora,* Boophilus spp., Rhipicephalus spp., Amblyomma spp., Hyalomma spp., Ixodes spp., Dermacentor spp., Haemaphysalis spp., Otobius spp., Psoroptes spp., Chorioptes spp., Sarcoptes spp., Psorergates spp., Demodex spp., Notoedres spp., Tarsonemus spp., *Bryobia praetiosa,* Panonychus spp. and Tetranychus spp..

The active compounds according to the invention are not only active against plant, hygiene and stored product pests, but also, in the veterinary medicine sector, against animal parasites (ectoparasites and endoparasites), such as ticks, ixodidae argasidae, scab mites, trombidae, flies (stinging and sucking), parasitic fly larvae, sucking lice, biting lice, bird lice, fleas and worms which live as endoparasites.

They are active against normally sensitive and resistant species and strains, as well as against all parasitic and non-parasitic stages of development of the ecto- and endo-parasites.

The active compounds according to the invention are distinguished by a strong insecticidal, acaricidal and ovicidal activity. They can be employed with particularly good success for combating insects which damage plants, for example against the green peach aphid (*Myzus persicae*) or against the larvae of the mustard beetle (*Phaedon cochleariae*) or against the larvae of the cabbage moth (*Plutella xylostella*) or against the larvae of the green rice leaf hopper (*Nephotettix cincticeps*) or against the larvae of the cotton ball worm (*Heliothis armigera*) or against the larvae of the full army worm (*Spodoptera frugiperda*); for combating mites which damage plants, such as, for example, against the common spider mite or the greenhouse spider mite (*Tetranychus urticae*), as well as ovicides, for example against the eggs of the cotton ball worm (*Heliothis armigera*). In addition, the new active compounds also show a good development-inhibitory action, for example in the case of the Mediterranean fruit fly (*Ceratitis capitata*).

In addition, they can be also employed with particularly good success for combating pests which live as parasites in warm-blooded animals, such as, for example, against the larvae of blow-flies (*Lucilia cuprina*), against cattle ticks (*Boophilus microplus*) or against sheep mange mites (*Psoroptes ovis*).

In the appropriate application rates, the active compounds according to the invention also show a good fungicidal action, such as, in particular, against *Pyricularia oryzae* in rice.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and-/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, mites, ticks etc. in the sector of animal keeping and cattle breeding; better results, for example higher milk production, greater weight, more attractive animal pelt, longer life, etc., can be achieved by combating the pests.

The active compounds are applied according to the invention in this sector in a known fashion, such as by external application in the form of, for example, dipping, spraying, pouring-on, spotting-on and dusting, as well as by parenteral application in the form, for example, of injection, and, furthermore, by means of the feed-through process. In addition, application as molded articles (collar, ear tag) and application in the form of the so-called environment treatment is also possible.

The biological effectiveness of the compounds according to the invention will be explained with reference to the examples below.

PREPARATION EXAMPLES

Example 1

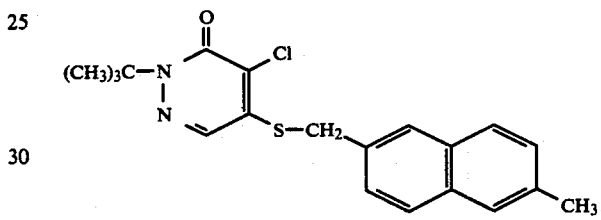

(Process a)

9.45 g (0.04 mol) of 2-bromomethyl-6-methylnaphthalene (cf., for example, Tetrahedron 34, 769–777 [1978]) are added to 8 g (0.03 mol) of 2-t-butyl-4-chloro-5-mercapto-3-pyridazin-(2H)-one (cf., for example, Japanese Patent 61/109,777) and 6.9 g (0.05 mol) of potassium carbonate in 50 ml of dimethylformamide, and the mixture is stirred for 16 hours at room temperature. For working up, the mixture is diluted with 250 ml of water and extracted twice with 80 ml of dichloromethane each time, the combined organic phases are dried over sodium sulphate and evaporated in vacuo, and the residue is purified by chromatography on silica gel (dichloromethane).

8.6 g (77% of theory) of 2-t-butyl-4-chloro-5-[(6-methyl-2-naphthyl)-methylthio]-3(2H)-pyridazinone of melting point 107° C. are obtained.

Example 2

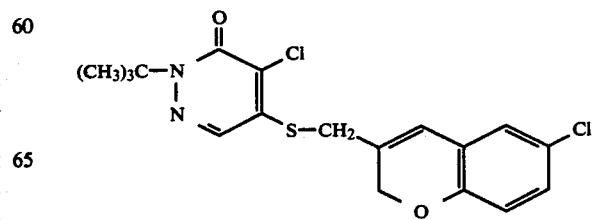

(Process a) 9.2 g (0.042 mol) of 6-chloro-3-chloro-methyl-2(H)-chromene are added, while cooling slightly, to a solution of 6.6 g (0.03 mol) of 2-t-butyl-4-chloro-5-mercapto-3-pyridazin-(2H) - one and 7.3 g (0.053 mol) of potassium carbonate in 50 ml of dimethylformamide and the mixture is stirred for 16 hours at room temperature. For working up the mixture is diluted with 250 ml of water and extracted twice, each time with 80 ml of dichloromethane, the combined organic phases are dried over sodium sulphate and evaporated in vacuo, and the residue is purified by chromatography on silica gel (dichloromethane). 8.2 g (68% of theory) of 2-t-butyl-4-chloro-5-[(6-chloro-2(H)-chromen-3-yl)-methylthio]-3(2H)-pyridazinone of a melting point of 82° C. are obtained.

PREPARATION OF THE STARTING PRODUCT

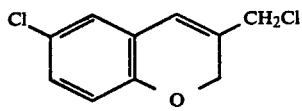

8.5 g (0.07 mol) of thionyl chloride are added dropwise to a solution of 9.8 g (0.045 mol) of 3-hydroxymethyl-6-chloro-2(H)-chromene in 50 ml of methylene chloride and the mixture is heated for 16 hours under reflux. After cooling, the reaction mixture is poured into 100 ml of water and the organic phase is separated off, washed twice with water, dried with sodium sulphate and evaporated. 9.2 g (95% of theory) of 3-chloromethyl-6-chloro-2(H)-chromene are obtained. 1H-NMR(CDCl₃):δ(ppm):4.15(S,2H), 4.83 (s, 2H),6.4(S,1H).

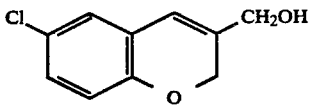

2.7 g (0.071mol) of lithium hydrides are added in portions to a solution of 20 g (0.095 mol) of 6-chloro-2(H)chromene-3-carbocylic acid in 150 ml of tetrahydrofuran and the mixture is then stirred for 16 hours at room temperature. For hydrolysis a mixture of 8 ml of ethyl acetate and 3 ml of water is added, while cooling with ice, and then a 5% strength sodium hydroxide solution is added until a filtrable, grey precipitate forms which is filtered off. The filtrate is evaporated, the residue is taken up in ether/water, and the organic phase is dried over sodium sulphate and evaporated 8.8 g (47% of theory) of 3-hydroxymethyl-6-chloro-2(H)-chromene are obtained. Mass spectrum: (e/z)=196/198 (30%/10%), 165/167 (100%/30%).

Example 3

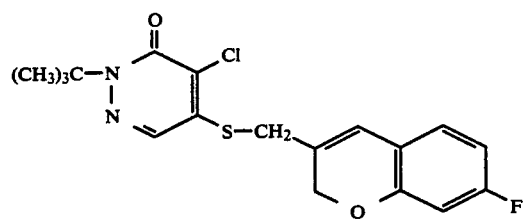

(Process a)

2-t-butyl-4-chloro-5-[(7-fluoro-2(H)-chromen-3-yl)-methylthio]-3(2H)-pyridazinone is obtained in accordance with Example 2.

1H-NMR(CDCl₃:δ(ppm)=4.81(s,2H); 3.25(s,2H);6,49(s,1H); 7.65(s,1H).

PREPARATION OF THE STARTING PRODUCT

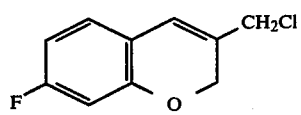

3-Chloromethyl-7-fluoro-2(H)-chromene is obtained in accordance with Example 2.

1H-NMR(CDCl₃):δ(ppm):4.15(s,2H);4.85(s,2H);6.45(s,1H).

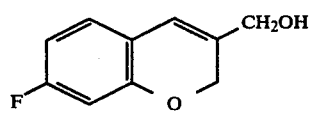

27.1 g (0.71 mol) of sodium borohydride are added in portions at 10°-20° C., while cooling with ice, to a solution of 36 g (0.2 mol) of 7-fluoro-2(H)-chromene-3-carbaldehyde in 250 ml of methanol and the mixture is stirred for 16 hours at room temperature. The reaction mixture is adjusted to a pH of 7-8 with 2N HCl and is evaporated. The residue is taken up in methylene chloride and washed with water, and the organic phase is dried and evaporated. 21 g (58% of theory) of 3-hydroxymethyl-7-fluoro-2(H)-chromene are obtained.

1H-NMR(CDCl₃, δ(ppm):4.18(s,2H).4.8(s,2H),1.85(broad,1H).

The following substituted pyridazinones of the general formula (I) are obtained in a corresponding manner and in accordance with the general preparation instructions:

Structure (I):

R¹-N-N=... pyridazinone with R², R³, R⁴, X, and a Z-containing bicyclic (R⁵, R⁶, R⁷, R⁸, R⁹) substituent.

| Ex. No. | R¹ | R² | R³ | R⁴ | X | Z-ring substituent | M.p. °C |
|---|---|---|---|---|---|---|---|
| 4 | (CH₃)₃C— | Cl | CH₃ | H | S | 1-Cl-2-methyl-naphthalenyl | 162 |
| 5 | (CH₃)₃C— | Cl | H | H | S | 6-tert-butyl-naphthalenyl | 127 |
| 6 | (CH₃)₃C— | Cl | H | H | S | 3-chloro-benzo[b]thiophenyl | 164 |
| 7 | (CH₃)₃C— | Cl | H | H | S | 1-chloro-2-methyl-naphthalenyl | 159 |
| 8 | (CH₃)₃C— | Cl | H | H | S | 2-methyl-naphthalenyl | 134 |
| 9 | (CH₃)₃C— | Cl | H | H | S | 6-CF₃-naphthalenyl | 103–104 |
| 10 | (CH₃)₃C— | Cl | H | H | S | 3-Cl-6-Br-benzo[b]thiophenyl | 87–88 |
| 11 | (CH₃)₃C— | Cl | H | H | S | 1-Br-2-methyl-naphthalenyl | 169 |
| 12 | (CH₃)₃C— | Cl | H | H | S | 1-Cl-2-methyl-6-COCH₃-naphthalenyl | 210–211 |

(I)

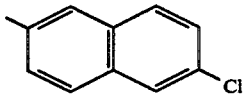

| Ex. No. | R¹ | R² | R³ | R⁴ | X | (aryl group) | M.p. °C |
|---|---|---|---|---|---|---|---|
| 13 | $(CH_3)_3C-$ | Cl | H | H | S | 3-chloro-benzo[b]thiophene with Cl | 154 |
| 14 | $(CH_3)_3C-$ | Cl | H | H | S | 6-chloro-naphthalen-2-yl | 64–65 |
| 15 | $(CH_3)_3C-$ | Cl | H | H | S | 1-chloro-2-methoxy-naphthalen-6-yl | 167 |
| 16 | $(CH_3)_3C-$ | Cl | H | H | S | 6-(difluoromethoxy)-naphthalen-2-yl | 102 |

USE EXAMPLES

In the Use Examples which follow, the compounds listed below were employed as comparison substances:

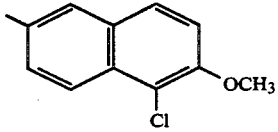

2-t-butyl-4-chloro-5-{2-[4-(3,3-dimethyl-butyl)-2,6-dichlorophenoxy]-ethylthio}-3(2H)-pyridazinone (known from European Patent 232,825)

(A)

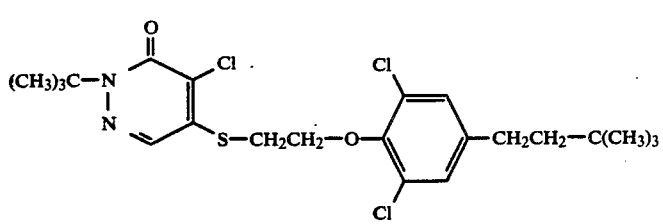

(B)

2-t-butyl-4-chloro-5-(4-t-butyl-phenylmethylthio)-3(2H)-pyridazinone (known from European Patent 134,439)

(C)

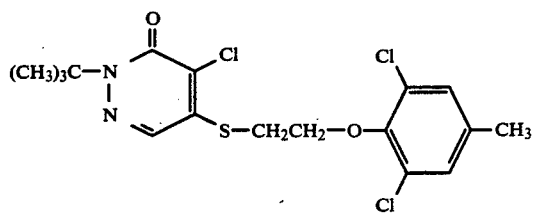

2-t-butyl-4-chloro-5-[2-(4-methyl-2,6-dichlorophenoxy)ethylthio]-3(2H)-pyridazinone (known from European Patent 232,825)

Example A

Test with *Boophilus microplus* resistant/Biarra strain, OP-resistant

Solvent:
35 parts by weight of ethylene glycol monomethyl ether
35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

10 adult Boophilus microplus res. are immersed for 1 minute in the active compound preparation to be tested. After transfer to plastic beakers and storage in a controlled-environment chamber, the degree of destruction is determined.

In this test, compound 1 of the Preparation Examples, for example, shows a superior action compared with the prior art.

Example B

Test with *Lucilia cuprina* resistant larvae

Emulsifier:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm$^3$ of horse meat and 0.5 ml of the preparation of active compound. After 24 hours, the degree of destruction is determined.

In this test, compound 1 of the Preparation Examples, for example, shows a superior action compared with the prior art.

Example C

Test with *Psoroptes ovis*

Solvent:
35 parts by weight of ethylene glycol monomethyl ether
35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

About 10–25 Psoroptes ovis are introduced into 1 ml of the active compound preparation to be tested, which has been pipetted into tablet nests of a deep-drawn pack. The degree of destruction is determined after 24 hours.

In this test, compound 1 of the Preparation Examples, for example, shows a superior action compared with the prior art.

Example D

Phaedon Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage plants (*Brassica oleracea*) are treated with the preparation of the active compound in the desired concentration. One leaf of the treated plant is placed in a plastic dish and larvae (L$_3$) of the mustard beetle (*Phaedon cochleariae*) are introduced. After 2 to 4 days, another leaf of the same plant is used each time for subsequent feeding.

After the desired time, the destruction is determined in %. In this test 100% means that all the animals have been destroyed; 0% means that none of the animals have been destroyed.

In this test, compound 1 of the Preparation Examples, for example, shows a superior action compared with the prior art.

Example E

Plutella Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage plants (*Brassica oleracea*) are treated with the preparation of the active compound in the desired concentration. One leaf of the treated plant is placed in a plastic dish and larvae (L$_2$) of the cabbage moth (*Plutella xylostella*) are introduced. After 2 to 4 days, another leaf of the same plant is used each time for subsequent feeding.

After the desired time, the destruction is determined in %. In this test 100% means that all the animals have been destroyed; 0% means that none of the animals have been destroyed.

In this test, compound 1 of the Preparation Examples, for example, shows a superior action compared with the prior art.

Example F

Spodoptera Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soy bean plants (*Glycine sova*) are treated with a preparation of the active compound in the desired concentration. In ten replications, one leaf of the treated plant is placed in each case in a plastic dish, and one larva (L$_2$) of the full army worm (*Spodoptera frugiperda*) is introduced per leaf. After 3 days, feeding is continued using a further leaf of the corresponding plant, depending on the dose. On day 7, the larvae are transferred to an untreated artificial diet.

After the desired time, the destruction is determined in %. In this test, 100% means that all the caterpillars have been destroyed; 0% means that none of the caterpillars have been destroyed.

In this test, compound 1 of the Preparation Examples, for example, shows a superior action compared with the prior art.

Example G

Heliothis Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya shoots (*Glycine soya*) are treated with a preparation of the active compound in the desired concentration. In ten replications, one leaf of the treated plant is placed in each case in a plastic dish, and one larva ($L_2$) of the cotton ball worm (*Heliothis armigera*) is introduced per dish. After 3 days, feeding is continued using a further leaf of the corresponding plant, depending on the dose. On day 7, the larvae are transferred to an untreated artificial diet.

After the desired time, the destruction is determined in %. In this test, 100% means that all the animals have been destroyed; 0% means that none of the animals have been destroyed.

In this test, compound 1 of the Preparation Examples, for example, shows a superior action compared with the prior art.

Example H

Development inhibition test with *Ceratitis capitata* (Mediterranean fruit fly)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

20 eggs of the Mediterranean fruit fly are placed in each case on a mush of artificial diet in a small dish. The diet is treated with the active compound in the indicated concentration. The destruction in % is calculated from the total of the destroyed eggs, larvae, pupae and adults, based on the number of eggs introduced.

In this test, 100% means that all animals have been destroyed; 0% means that none of the animals have been destroyed.

In this test, compound 1 of the Preparation Examples, for example, shows a superior action compared with the prior art.

Example I

Nephotettix Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration, and green rice leaf hoppers (*Nephotettix cincticeps*) are placed on them.

After the desired time, the destruction is determined in %. In this test, 100% means that all leaf hoppers have been destroyed; 0% means that none of the leaf hoppers have been destroyed.

In this test, compound 1 of the Preparation Examples, for example, shows a superior action compared with the prior art.

Example J

Myzus Test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested with the green peach aphid (*Myzus persicae*) are treated by being dipped into a preparation of the active compound in the desired concentration.

After the desired time, the destruction is determined in %. In this test, 100% means that all aphids have been destroyed; 0% means that none of the aphids have been destroyed.

In this test, compound 1 of the Preparation Examples, for example, shows a superior action compared with the prior art.

Example K

Ovicidal action on egg clusters of *Heliothis armigera* (cotton ball worm)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

2-day old clusters of eggs on filter paper were immersed for 30 seconds in preparations of the active compound in the desired concentration, placed in sealed Petri dishes and kept in the laboratory for 6 days under long-day conditions. The criterion for assessing the effect was the hatching inhibition in percent compared with untreated egg clusters.

In this test, compound 1 of the Preparation Examples, for example, shows a superior action compared to the prior art.

Example L

Tetranychus Test (OP-resistant)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the common spider mite or greenhouse spider mite (*Tetranychus urticae*) are sprayed with a preparation of the active compound in the desired concentration until dripping wet.

After the desired time, the destruction is determined in %. In this test, 100% means that all spider mites have been destroyed; 0% means that none of the spider mites have been destroyed.

In this test, compound 1 of the Preparation Examples, for example, shows a superior action compared with the prior art.

It will be appreciated that the instant specification and claims are set forth by way of illustration and not limitation, and that various modifications and changes may be made without departing from the spirit and scope of the present invention.

What is claimed is:

1. A substituted pyridazinone of the formula

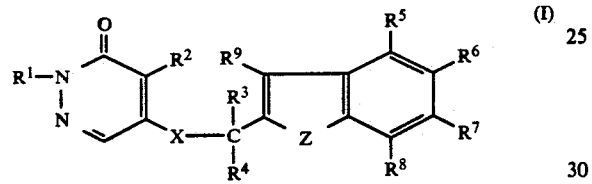

in which
- $R^1$ represents straight-chain or branched alkyl having 1 to 8 carbon atoms; or represents straight-chain or branched halogenoalkyl having 1 to 6 carbon atoms and 1 to 13 identical or different halogen atoms, or represents cycloalkyl which has 3 to 7 carbon atoms or cycloalkylalkyl which has 3 to 7 carbon atoms in the cycloalkyl moiety and 1 to 4 carbon atoms in the straight-chain or branched alkyl moiety, each of which is optionally substituted on the cycloalkyl moiety by at least one substituent selected from the group consisting of alkyl having 1 to 4 carbon atoms and halogen; or represents aralkyl which has 6 to 10 carbon atoms in the aryl moiety and 1 to 4 carbon atoms in the straight-chain or branched alkyl moiety and which is optionally substituted on the aryl by at least one radical selected from the group consisting of halogen, cyano, nitro, in each case straight-chain or branched alkyl, alkoxy or alkylthio, each of which has 1 to 4 carbon atoms, or in each case straight-chain or branched halogenoalkyl, halogenoalkoxy or halogenoalkylthio, each of which has 1 to 4 carbon atoms and 1 to 9 identical or different halogen atoms,
- $R^2$ represents fluorine, chlorine, bromine or iodine, or represents straight-chain or branched alkyl having 1 to 4 carbon atoms,
- $R^3$ and $R^4$ independently of one another each represents hydrogen, or represents straight-chain or branched alkyl having 1 to 4 carbon atoms,
- $R^5$, $R^6$, $R^7$, $R^8$ and $R^9$ independently of one another each represents hydrogen or halogen or represent in each case straight-chain or branched alkyl, alkoxy or alkylthio, each of which has 1 to 4 carbon atoms, or represent in each case straight-chain or branched halogenoalkyl, halogenoalkoxy or halogenoalkylthio, each of which has 1 to 4 carbon atoms and each of which has 1 to 9 identical or different halogen atoms,
- X represents oxygen or sulphur and
- Z represents a radical of the formula —CH=CH—, —CH$_2$—O—, —O— or —S—.

2. A substituted pyridazinone according to claim 1, in which
- $R^1$ represents methyl, ethyl, n- or i-propyl or n-, i-, s- or t-butyl, or represents straight-chain or branched pentyl, or represents straight-chain or branched hexyl, or represents straight-chain or branched fluoroalkyl having 1 to 4 carbon atoms and 1 to 5 fluorine atoms, or represents cyclopropyl, cyclopentyl, cyclohexyl, cyclopropylmethyl, cyclopropylethyl, cyclopropylpropyl or cyclohexylmethyl, each of which is optionally monosubstituted to pentasubstituted by identical or different substituents selected from the group consisting of fluorine, chlorine, methyl and ethyl, or represents benzyl which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy or trifluoromethylthio,
- $R^2$ represents fluorine, chlorine, bromine, methyl, ethyl or n- or i-propyl,
- $R^3$ and $R^4$ independently of one another each represents hydrogen, methyl or ethyl,
- $R^5$, $R^6$, $R^7$, $R^8$ and $R^9$ independently of one another each represents hydrogen, fluorine, chlorine, bromine, iodine, methyl, ethyl, n- or i-propyl, n-, i-, s- or t-butyl, trifluoromethyl, trifluoromethoxy, difluoromethoxy, trifluoromethylthio, methoxy, ethoxy or methylthio,
- X represents a radical of the formula —CH=CH—, —CH$_2$—O—, —O— or —S—.

3. A substituted pyridazinone according to claim 1, in which
- $R^1$ represents methyl, ethyl, i-propyl, i-butyl, t-butyl, i-amyl, t-amyl, difluoro-t-butyl- or trifluoro-t-butyl, or represents cyclopentyl or cyclohexyl, or represents cyclopropylmethyl or cyclopropylethyl, each of which is optionally monosubstituted to pentasubstituted by identical or different substituents from the group consisting of fluorine, chlorine and methyl, or represents benzyl which is optionally monosubstituted or disubstituted by identical or different substituents from the group consisting of fluorine, chlorine, bromine, methyl, ethyl, methoxy, methylthio, trifluoromethyl, trifluoromethoxy, difluoromethoxy and trifluoromethylthio,
- $R^2$ represents chlorine, bromine, methyl or ethyl,
- $R^3$ and $R^4$ independently of one another each represents hydrogen or methyl,
- $R^5$, $R^6$, $R^7$, $R^8$ and $R^9$ independently of one another each represents hydrogen, fluorine, chlorine, bromine, methyl, ethyl, trifluoromethoxy, n-, i-, s- or t-butyl, trifluoromethyl, difluoromethoxy, trifluoromethylthio, methoxy or ethoxy,
- X represents oxygen or sulphur and
- Z represents a radical of the formula —CH=CH—, —CH$_2$—O—, —O— or —S—.

4. A substituted pyridazinone according to claim 3, in which Z represents a radical of the formula —CH$_2$—O—.

5. A compound according to claim 1, wherein such compound is 2-t-butyl-4-chloro-5-[(6-methyl-2-naphthyl)-methylthio]-3(2H)-pyridazinone of the formula

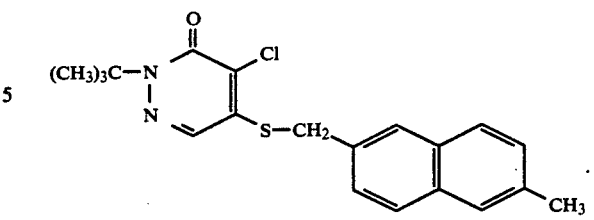

6. A pesticidal composition comprising a pesticidally effective amount of a compound according to claim 1 and a diluent.

7. A method of combating pests which comprises applying thereto or to a habitat from which it is desired to exclude them a pesticidally effective amount of a compound according to claim 1.

* * * * *

UNITED STATES PATENT AND TRADEMARK OFFICE
CERTIFICATE OF CORRECTION

PATENT NO. : 5,004,744

DATED : April 2, 1991

INVENTOR(S) : Weissmuller et al.

It is certified that error appears in the above-identified patent and that said Letters Patent is hereby corrected as shown below:

Col. 30, lines 40-41  After " represents " delete " a radical of the formula $-CH=CH-$, $-CH_2-O$, $-O-$ or $-S-$. " and substitute -- oxygen or sulphur and --

Col. 30, line 41  Insert -- Z represents a radical of the formula $-CH=CH-$, $-CH_2-O-$, $-O-$ or $-S-$. --

Signed and Sealed this

Twelfth Day of January, 1993

*Attest:*

DOUGLAS B. COMER

*Attesting Officer*  *Acting Commissioner of Patents and Trademarks*